(12) United States Patent
Schmieding et al.

(10) Patent No.: US 8,038,678 B2
(45) Date of Patent: Oct. 18, 2011

(54) ARTHROSCOPIC UNICOMPARTMENTAL KNEE AND METHOD OF FORMATION

(75) Inventors: Reinhold Schmieding, Naples, FL (US); Ricardo Albertorio, Naples, FL (US); Jacob Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 703 days.

(21) Appl. No.: 11/740,198

(22) Filed: Apr. 25, 2007

(65) Prior Publication Data

US 2008/0039852 A1 Feb. 14, 2008

Related U.S. Application Data

(60) Provisional application No. 60/794,511, filed on Apr. 25, 2006.

(51) Int. Cl.
*A61B 17/16* (2006.01)
(52) U.S. Cl. ........................................ 606/80; 623/20.3
(58) Field of Classification Search .................... 606/80, 606/96, 98, 88, 79, 86 R; 623/13.11–13.14, 623/20.1, 20.3
See application file for complete search history.

(56) References Cited

U.S. PATENT DOCUMENTS

| | | | | |
|---|---|---|---|---|
| 4,105,055 | A * | 8/1978 | Brenta | 144/286.1 |
| 5,306,301 | A * | 4/1994 | Graf et al. | 606/232 |
| 5,320,115 | A * | 6/1994 | Kenna | 128/898 |
| 5,374,269 | A * | 12/1994 | Rosenberg | 606/80 |
| 6,015,411 | A * | 1/2000 | Ohkoshi et al. | 606/80 |
| 6,197,064 | B1 * | 3/2001 | Haines et al. | 623/20.31 |
| 6,482,209 | B1 * | 11/2002 | Engh et al. | 606/79 |
| 6,554,838 | B2 * | 4/2003 | McGovern et al. | 606/87 |
| 7,520,901 | B2 * | 4/2009 | Engh et al. | 623/20.21 |
| 2004/0176771 | A1 * | 9/2004 | Schmieding | 606/80 |
| 2004/0199166 | A1 * | 10/2004 | Schmieding et al. | 606/79 |
| 2005/0192588 | A1 * | 9/2005 | Garcia | 606/88 |
| 2005/0283160 | A1 * | 12/2005 | Knisely et al. | 606/80 |
| 2007/0233128 | A1 | 10/2007 | Schmieding et al. | |
| 2007/0250067 | A1 | 10/2007 | Schmieding et al. | |

* cited by examiner

*Primary Examiner* — Thomas C. Barrett
*Assistant Examiner* — Christian Sevilla
(74) *Attorney, Agent, or Firm* — Dickstein Shapiro LLP

(57) ABSTRACT

A two sided cylindrical chondral resurfacing implant that covers areas of the highest contact between the tibia and femur. A dual-sided rotary drill cutter is employed to create a tibial socket from outside in. A full femoral trough is made with the opposite side of the rotary drill cutter by simply moving the knee through flexion and extension. In this manner, automatic alignment of femoral and tibial components is achieved due to the "transtibial" nature of the femoral preparation.

22 Claims, 7 Drawing Sheets

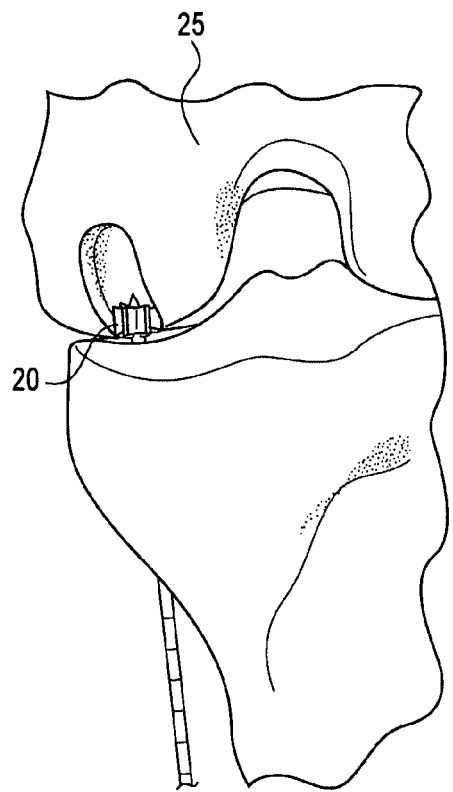
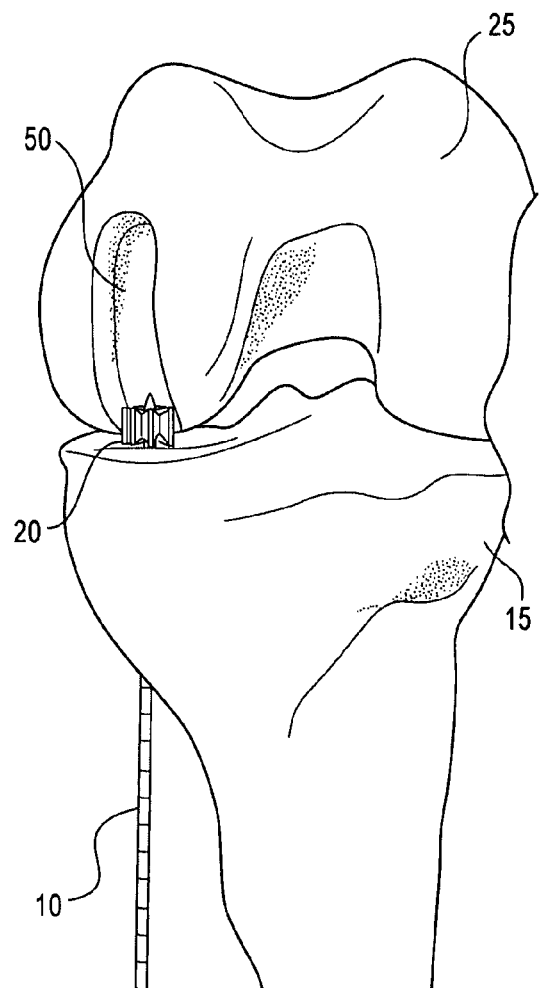
FIG. 3
FIG. 4

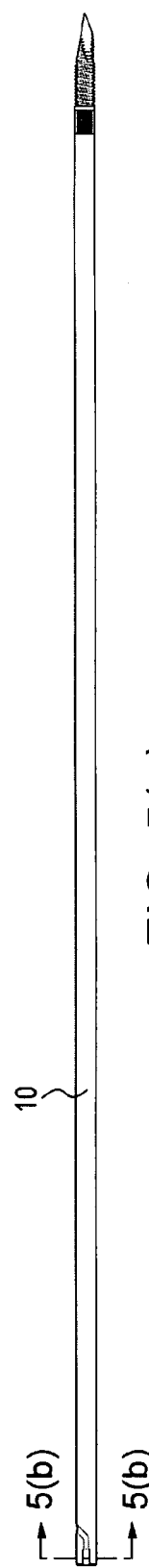
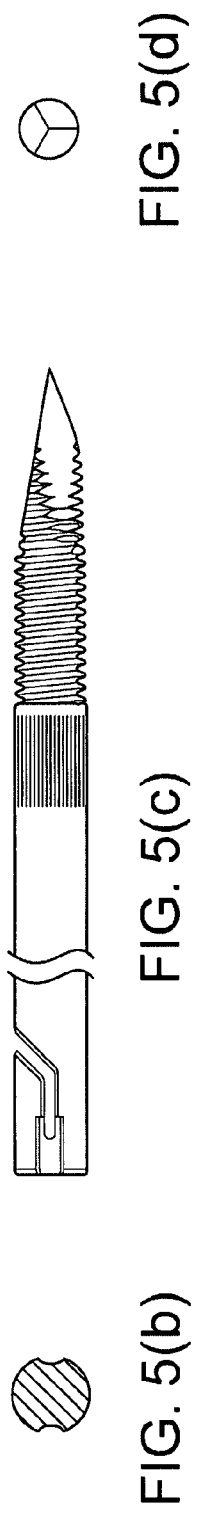
FIG. 5(a)
FIG. 5(b)
FIG. 5(c)
FIG. 5(d)

ARTHROSCOPIC UNICOMPARTMENTAL KNEE AND METHOD OF FORMATION

CROSS-REFERENCE TO RELATED APPLICATIONS

This application claims the benefit of U.S. Provisional Application No. 60/794,511, filed Apr. 25, 2006, the entire disclosure of which is incorporated by reference herein.

FIELD OF THE INVENTION

The present invention relates to the field of arthroscopic surgery and, more particularly, to methods of reconstructive knee surgery.

BACKGROUND OF THE INVENTION

Partial knee replacement surgery, also called unicompartmental knee arthroplasty, is routinely considered for the treatment of osteoarthritis of the knee joint. Partial knee replacement surgery has generated significant interest because it entails a smaller incision and faster recovery than traditional total joint replacement surgery.

When partial knee replacement is performed, the bone and cartilage on the end of the femur and top of the tibia are removed. This is performed using precise instruments to create exact surfaces to accommodate the implant. A knee replacement implant made of various biocompatible materials such as metal or plastic is then, placed to function as a new knee joint. Depending on the condition of the cartilage on the undersurface of the kneecap, this may also be replaced. The knee replacement implant typically comprises (i) a femoral component, made of metal and which fits on the femur, (ii) a tibial component, made of metal and which fits on the tibia, (iii) a patellar component, made of plastic and which replaces the cartilage on the undersurface of the kneecap, and (iv) a plastic insert which fits between the femoral and tibial components.

SUMMARY OF THE INVENTION

The present invention provides techniques and apparatus for knee replacement surgery by utilizing a cutter (for example, a dual sided rotary drill cutter) to cut the tibial tunnel in a retrograde manner, and to form at least one cut on the femur through at least one flexion/extension motion of the knee and by employing the cutter.

In an exemplary embodiment, the invention provides a two sided cylindrical chondral resurfacing implant that covers areas of the highest contact between the tibia and femur. A cutter (for example, a dual sided rotary drill cutter) is employed to create a tibial socket from outside in. A full femoral through is then made with the opposite side of the cutter by simply moving the knee through flexion and extension. In this manner, automatic alignment of femoral and tibial components is achieved due to the "transtibial" nature of the femoral preparation.

The present invention also provides a method of arthroscopically preparing both the femur and tibia to accept a unicompartmental implant that covers the entire contact area between femur and tibia. The method comprises the steps of: (i) forming a tibial socket in a retrograde manner by employing a first side of a cutter (for example, a dual sided rotary drill cutter); (ii) performing at least one cut on the femoral condyle with the cutter, by moving the knee through flexion/extension so that the femoral cut is directly aligned with the load bearing axis of the tibia; and (iii) placing an implant over the tibial socket and the femoral cut.

Although the present invention is described below in correction with a unicompartmental knee procedure, the invention can also advantageously be used for similar procedures in other joints other than the knee.

Other features and advantages of the present invention will become apparent from the following description of the invention which refers to the accompanying drawings.

BRIEF DESCRIPTION OF THE DRAWINGS

FIG. 3 illustrates the knee of FIG. 1 at a step subsequent to that of FIG. 2;

FIG. 4 illustrates the knee of FIG. 1 at a step subsequent to that of FIG. 3;

FIG. 5(a)-(d) illustrate various views of a guide pin employed for the knee replacement surgery of the present invention;

DETAILED DESCRIPTION OF THE INVENTION

Figure 1:
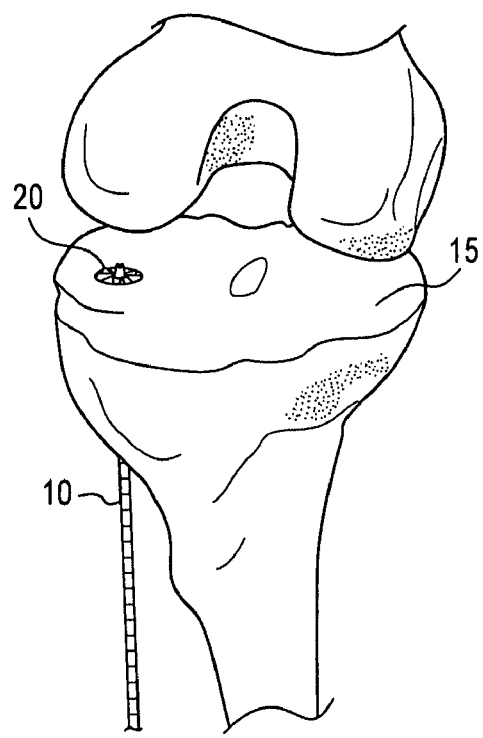
FIG. 1 illustrates a schematic view of a knee undergoing knee replacement surgery according to an embodiment of the present invention.

Referring now to the drawings where like elements are designated by like reference numerals, FIGS. 1-4 illustrate a method of arthroscopically preparing both the femur and the tibia to accept a unicompartmental implant that covers a portion of the contact area between femur and tibia. As described below, the method comprises the steps of: (i) forming a tibial socket in a retrograde manner by employing a first side of a cutter or cutting instrument (for example, a dual sided rotary drill cutter); (ii) performing at least one cut on the femoral condyle with the cutter (for example, with a second side of the dual sided rotary drill), by advancing the cutter into the femur and moving the knee through flexion/extension so that the femoral cut is directly aligned with the load bearing axis of the tibia; and (iii) placing an implant over the tibial socket and the femoral cut.

According to an exemplary method of the present invention, an opening wedge osteotomy may be first conducted to correct any alignment deficiencies and to release the MCL to gain access to the medial joint space. The leg is flexed to a maximum load bearing angle, to arthroscopically optimize contact of femoral and tibial damaged surfaces. Using an arthroscopic drill guide that ensures a 90 degree angle pin entry to articulating surfaces, a 4 mm diameter guide pin 10 is drilled into the center of the femoral defect with placement into the center of the tibial defect confirmed.

Figure 2:
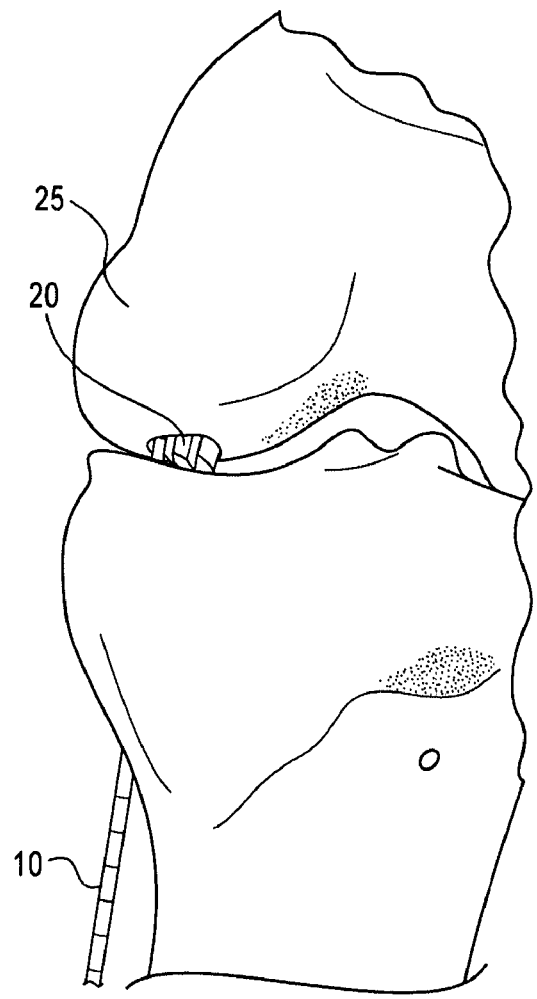
FIG. 2 illustrates another view of the knee of FIG. 1 at a method step subsequent to that of FIG. 1.

FIGS. 1 and 2 illustrate guide pin 10, which has been drilled outside-in using a C-Ring Guide that also acts as a template for tibial implant sizing (not shown). A dual sided rotary drill cutter 20 is inserted into the joint and threaded onto the pin tip arthroscopically in a manner similar to the insertion of the rotary drill in the technique for ACL Retro-Construction by Arthrex, Inc., Naples, Fla., and disclosed in U.S. application Ser. No. 11/598,093, filed on Nov. 13, 2006, the disclosure of which is incorporated in its entirety by reference herein. As described and claimed in U.S. application Ser. No. 11/598,093, the rotary drill insertion technique involves threading an appropriate diameter rotary drill cutter 20 onto an insertion post connected to a C-Ring, inserting the mounted rotary drill cutter into the knee joint through the anteromedial portal, and advancing the drill, pin through a guide sleeve connected to the C-Ring, through the tibia and into the joint to engage the cutter.

The diameter of the rotary drill cutter 20 may be, for example, 15, 20 or 25 mm, with a 5 mm thickness. The guide pin 10 and the sharp disposable cutter create a very clean socket in the tibia up to the depth of the implant, as described in more detail below.

A tibial socket is made in tibia 15 by drilling and pulling distally and using a first side of the rotary drill cutter 20. The tibial socket matches in angle and alignment at the optimum knee flexion angle.

Figure 6A:
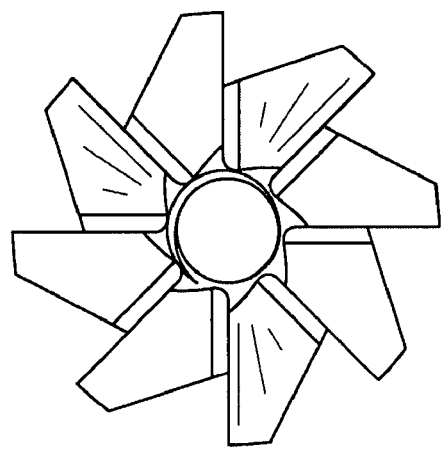
FIG. 6(a)-(c) illustrate various views of a rotary drill cutter employed in conjunction with the guide pin of FIG. 5(a)-(d)
Figure 6B:
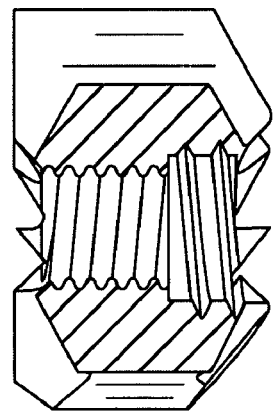
Figure 6C:
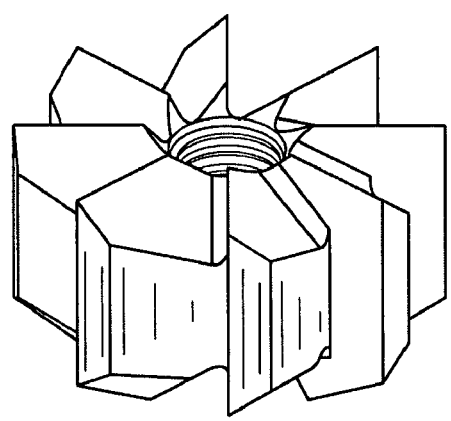

Details of a 3 mm guide pin 10 are illustrated in FIGS. 5(a)-(d). FIGS. 6(a)-(c) illustrate the dual-sided rotary drill cutter 20 in more detail. Advantageously, the dual-sided rotary drill cutter 20 has cutting flutes on both sides of the cutter. Slow forward drilling of the guide pin 10 engages the cutter 20 onto the guide pin 10 and simultaneously disengages the cutter from the threaded insertion post. Details of the rotary drill cutter 20 and of methods of creating bone sockets in a retrograde manner using the rotary drill cutter 20 are described in U.S. application Ser. No. 11/723,511, filed on Mar. 20, 2007, the disclosure of which is incorporated by reference in its entirety.

Referring now to FIG. 2, a second side (preferably opposite to the first side) of the dual sided rotary drill cutter 20 is employed to make a series of plunge cuts on the femoral condyle 25. The entire femoral condyle 25 is easily accessed by moving the knee through flexion/extension. The femoral cuts are directly aligned on the load bearing axis with the tibia since a "transtibial approach" is used.

As illustrated in FIGS. 3 and 4, after making plunge cuts on femoral condyle 25, the dual retrocutter continues on forward drilling and the knee is cycled through flexion/extension to smooth edges and complete femoral cut 50. In this manner, a full femoral trough can be made by simply moving the knee through flexion and extension. This method arthroscopically prepares both the femur and tibia to accept a more standard appearing unicompartmental implant that covers a portion of the contact area between femur and tibia. One key benefit of this procedure is the automatic alignment of femoral and tibial components due to the "transtibial" nature of the femoral preparation.

After completing the cuts, femoral and tibial implants can be pulled into place with FiberWire through transosseous holes. Cement may be injected through the holes to prepare a mantel over which the implant is placed. External guides may be used for targeting pin placement and to guide milling of sockets (angles). Femoral implants may be cemented, press fit, and/or made up of one or more interlocking pieces. Material may be cobalt chrome alloy or similar compositions. Tibial components may be press fit or cemented and/or made of polymer (machined or compression molded). Tibial components may also be metal backed. For added fixation, the femoral and/or tibial components may be secured with buttons or screws.

Figure 7:
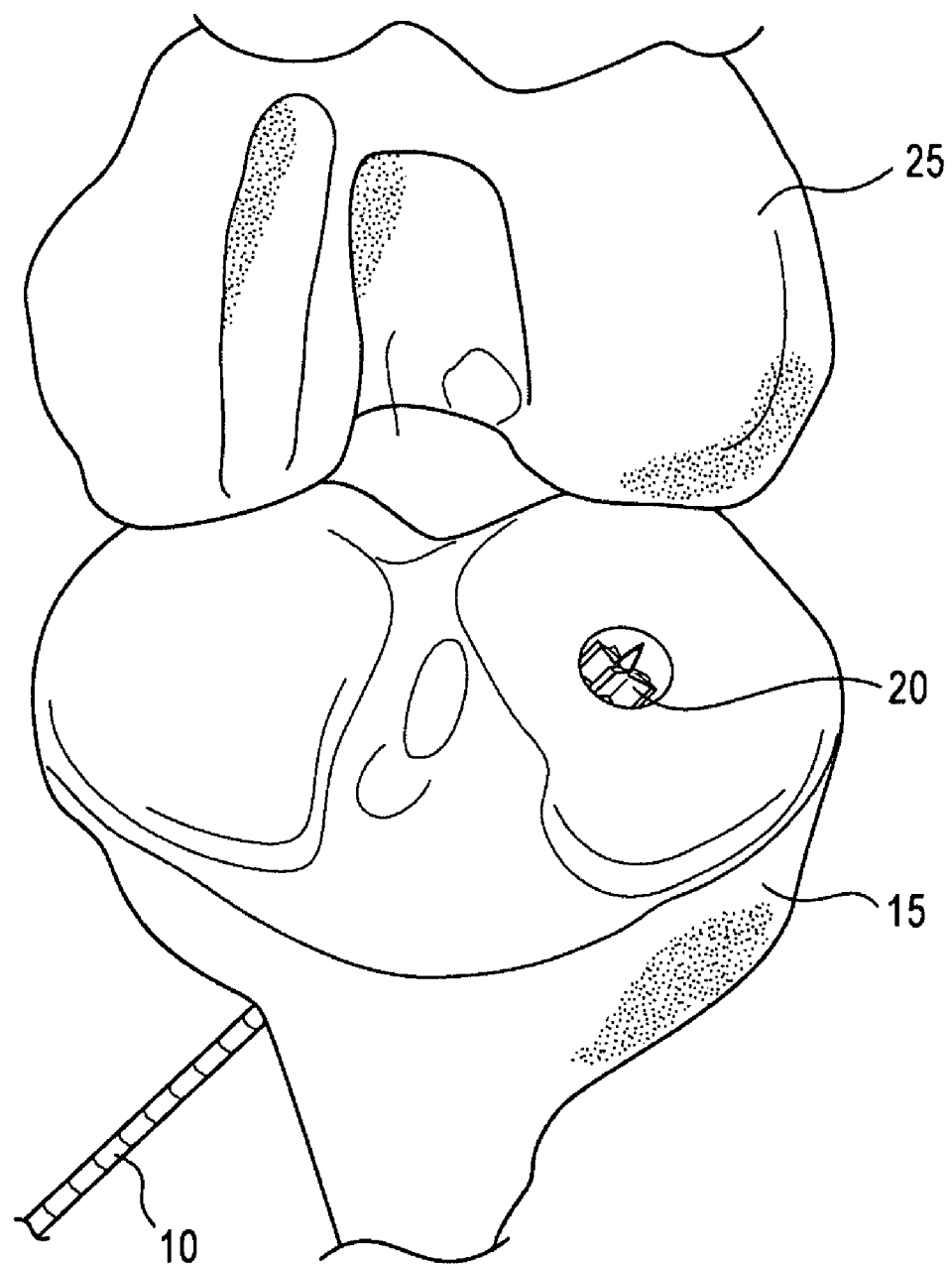
FIG. 7 illustrates a schematic view of a knee undergoing knee replacement surgery according to another embodiment of the present invention.
Figure 8:
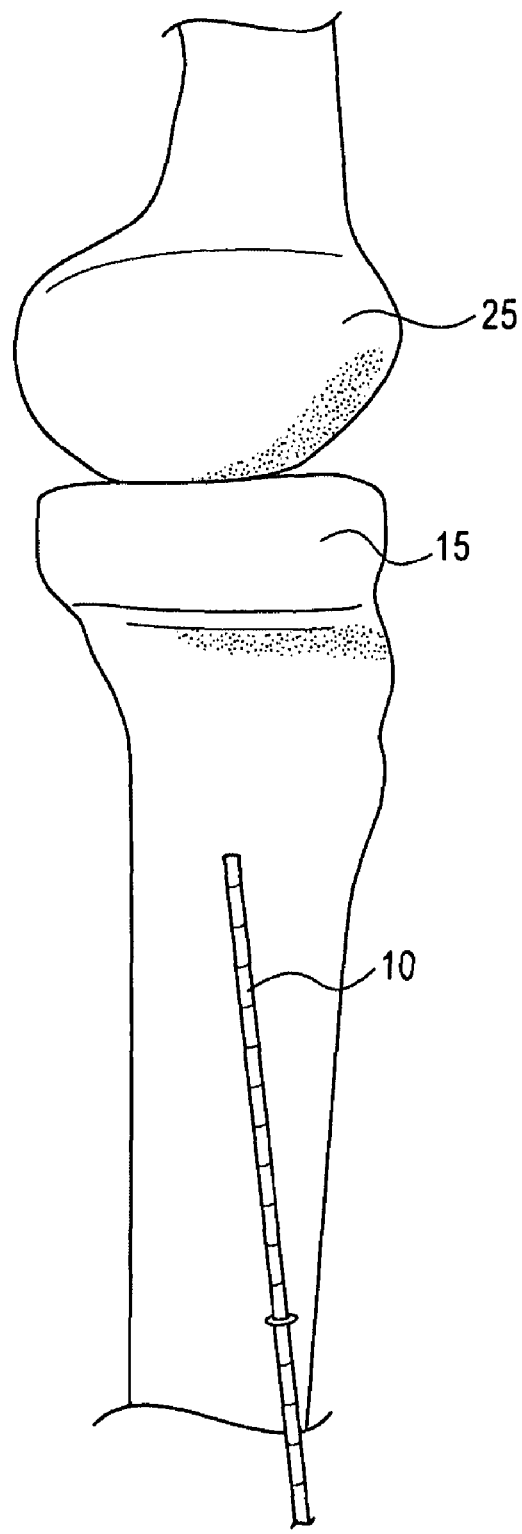
FIG. 8 illustrates a lateral view of the knee of FIG. 7.
Figure 9:
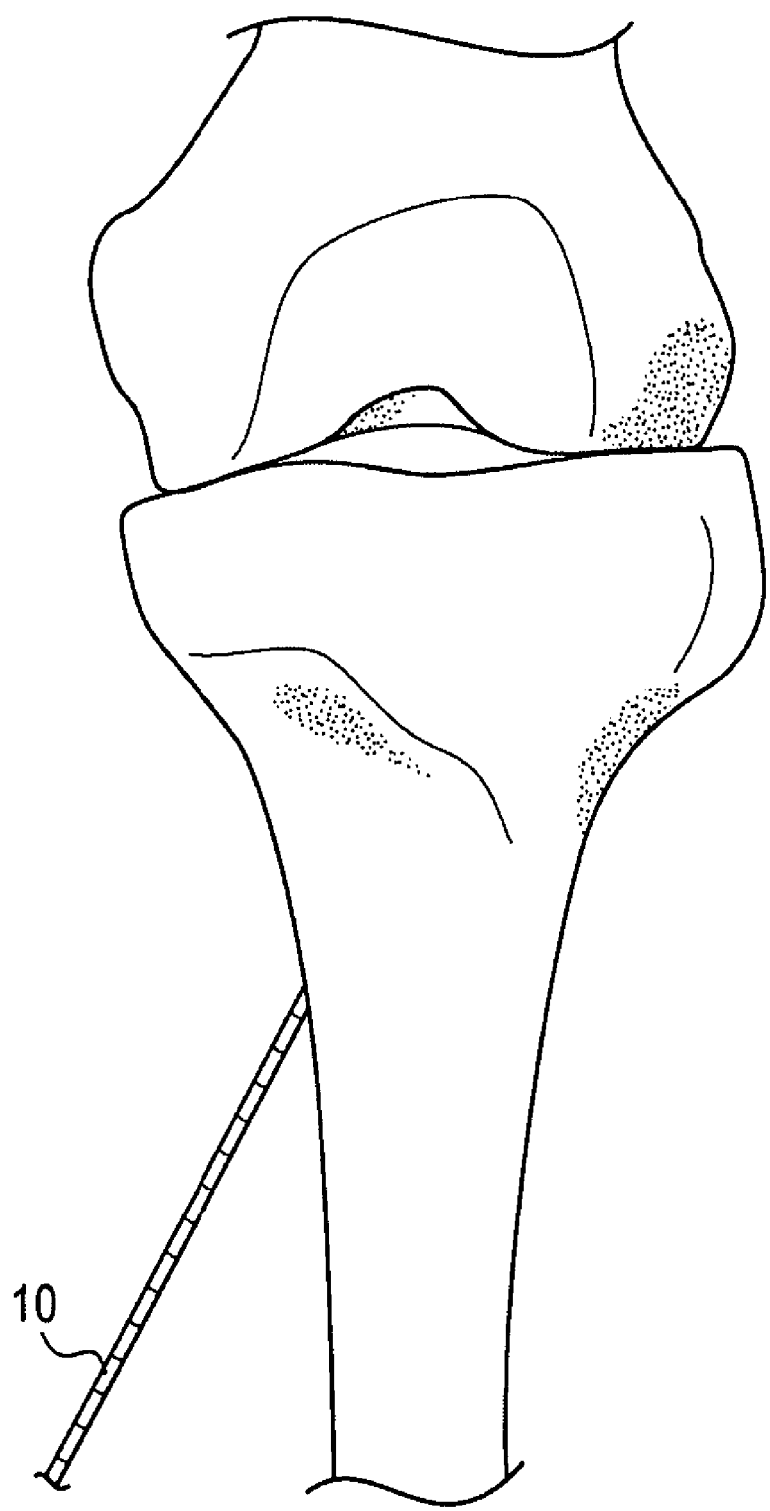
FIG. 9 illustrates another view of the knee of FIG. 7.

Although the above-detailed method has been described with reference to a specific embodiment according to which the drill guide pin 10 is drilled outside-in using a C-Ring Guide, in a lateral manner, as shown in FIGS. 1 and 2, for example, the invention is not limited to this particular exemplary embodiment and contemplates additional embodiments according to which drilling of the guide pin may be conducted at different orientations relative to the tibial plateau. For example, FIGS. 7-9 illustrate another method of arthroscopically preparing both the femur and the tibia to accept a unicompartmental implant, according to which the guide pin 10 is oriented and drilled in a cross-over manner to prepare the medial compartment. This embodiment has particular applications to medial compartment applications, since about 85% of early stage bone and cartilage knee damage occurs at this point.

In the cross-over embodiment, the guide pin 10 is oriented on the opposite side of the knee, to place the rotary drill clutter 20 about perpendicular to the tibiofemoral surfaces and to subsequently achieve a corresponding trough on the femoral side. In this manner, pin placement for the medial plateau is more manageable and the anatomic sloping of both the antero-posterior and medial-lateral surfaces of the tibia may be used to surgeon's advantage.

In certain applications, separate cutters for femur and tibia may be necessary with smooth, slightly convex back sides to protect opposing surfaces during retrograde drilling and to ease insertion through a small anterior incision. A very thin, flexible, plastic disc could be optionally employed to be cover the cutting flutes during insertion and to be pulled off the cutter with a traction suture attached to it after the cutter is in place and engaged on the pin. A radial slot in the disc on the opposite side of the traction suture would allow easy separation from the cutter and pin.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly it is not intended that the present invention be limited to the illustrated embodiments, but only by the appended claims.

What is claimed as new and desired to be protected by Letters Patent of the United States is:

1. A method of knee reconstruction comprising:
    forming a socket in a tibia in a retrograde manner using a rotary drill cutter;
    moving the knee through flexion/extension to engage the rotary drill cutter against a femur of the knee to cut into the femur and to remove at least a part of an articular femoral surface in an antegrade manner.

2. The method of claim 1, wherein the part of the articular femoral surface that is removed is directly aligned with a load bearing axis of the tibia.

3. The method of claim 1, further comprising the step of securing at least one of a tibial and femoral implant in the socket and the articular femoral surface.

4. The method of claim 1, wherein the rotary drill cutter is a dual-sided rotary drill cutter.

5. The method of claim 1, wherein the rotary drill cutter comprises two opposed sides and is provided with cutting surfaces on both sides, such that the rotary drill cutter is configured for cutting in two directions.

6. The method of claim 1, wherein the rotary drill cutter comprises a cannulation.

7. The method of claim 6, wherein the cannulation is threaded.

8. The method of claim 7, wherein the cannulation is threaded such that forward drilling engages the rotary drill cutter to a drill pin.

9. The method of claim 1, wherein the step of forming a socket in the tibia further comprises:
introducing a guide pin through the tibia;
attaching the cutter to the guide pin; and
retrograde cutting into the tibia to form the socket in the tibia.

10. The method of claim 1, wherein the step of removing at least a part of an articular femoral surface further comprises:
introducing a guide pin through the tibia;
attaching the dual-sided rotary drill cutter to the guide pin;
aligning the guide pin; and
moving the knee through at least a flexion or an extension to cut into the femur to form a femoral trough.

11. A method of bone reconstruction comprising:
providing a socket in a first bone in a retrograde manner using a first cutting side of a rotary drill cutter, the first bone normally articulating in a predetermined manner with a second bone at an articular joint; and
without removing or reorienting the rotary drill cutter in the articular joint, removing at least a part of an articular surface of the second bone in an antegrade manner using a second cutting side of the rotary drill cutter while moving the articular joint through flexion or extension.

12. The method of claim 11, wherein the part of the articular surface of the second bone that is removed is directly aligned with a weight bearing axis of the first bone.

13. The method of claim 11, wherein the first bone is tibia and the second bone is femur.

14. The method of claim 11, further comprising the step of securing at least a subcomponent of an implant in the socket of the first bone and the articular surface of the second bone.

15. The method of claim 11, wherein the rotary drill cutter comprises a cannulation and a plurality of cutting teeth oriented symmetrically relative to a longitudinal axis of the cutter.

16. The method of claim 11, wherein the rotary drill cutter comprises two opposed sides and is provided with cutting surfaces on both sides, such that the rotary drill cutter is configured for cutting in two directions.

17. A method of bone reconstruction comprising:
forming a socket in a first bone by conducting a first action using a first cutting side of a rotary drill cutter, the first bone normally articulating in a predetermined manner with a second bone;
removing tissue from the second bone by using a second cutting side of the rotary drill cutter and by conducting a second action which is different from the first action and without removing or reorienting the rotary, drill cutter; and
securing a bone implant between the socket in the first bone and the second bone; wherein the first action comprises drilling and the second action comprises flexing or extending the second bone.

18. The method of claim 17, wherein the first action is conducted in a first direction, and the second action is conducted in a second direction which is different from the first direction.

19. The method of claim 17, wherein the rotary drill cutter comprises two opposed sides and is provided with cutting surfaces on both sides, such that the rotary drill cutter is configured for cutting in two directions.

20. The method of claim 17, wherein the first bone is tibia and the second bone is femur.

21. A method of knee reconstruction comprising:
inserting a guide pin through a tibia;
attaching a dual-sided rotary drill cutter to the guide pin;
forming a tibial socket in the tibia by retrograde drilling using a first cutting side of the dual-sided rotary drill cutter;
forming at least one cut on the femoral condyle using a second cutting side of the dual-sided rotary drill cutting, by flexing or extending the knee, wherein the dual-sided rotary drill cutter is not removed from the joint or reoriented in the joint between formation of the socket and of the at least one cut; and
securing at least a subcomponent of a knee implant in the cut in the femoral condyle or the socket of the tibia.

22. The method of claim 21, wherein the dual-sided rotary drill cutter comprises two opposed sides and is provided with cutting surfaces on both sides, such that the rotary drill cutter is configured for cutting in two directions.

* * * * *